United States Patent [19]

Klemm

[11] Patent Number: Plant 7,014

[45] Date of Patent: Sep. 5, 1989

[54] GERANIUM PLANT NAMED MAPURSIT

[76] Inventor: Siegfried Klemm, Hanfacker 8, D-7000 Stuttgart 50, Fed. Rep. of Germany

[21] Appl. No.: 241,097

[22] Filed: Sep. 6, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new geranium cultivar distinguished by its sturdy, round and long lasting flower clusters standing on 14 cm. long, light brown stalks, each containing about sixty-five florets of medium size and salmon coloration, each floret having seven or eight, wide, regularly imbricated petals forming a closed cap and having an overall salmon coloration whereby the flower cluster provides a solid bright pink presentation; by its bushy, compact growth habit with good strength and a medium growth rate; and by its abundant, profusely produced foliage, of relatively small leaves, which stands about 20 cm. above the soil.

1 Drawing Sheet

BACKGROUND OF THE NEW PLANT

This new geranium plant originated as a seedling of the geranium variety 'Fledermaus' (U.S. Plant Pat. No. 5,368) growing in my nursery at Stuttgart, West Germany, and randomly pollinated with the object of seed collection, my new variety of geranium being selected from a group of plants grown from seeds of the said seed parent. This selected plant as asexually reproduced by me and under my direction at Stuttgart by means of cuttings, with such favorable results that continued propagation by cuttings was carried on at Stuttgart through several successive generations, which demonstrated that the novel and desirable characteristics would hold true from generation to generation and appeared to be firmly fixed. This new variety is now being grown for commercial purposes at my nursery at Stuttgart, West Germany.

DESCRIPTION OF THE DRAWING

This new geranium cultivar is illustrated by the accompanying photographic drawing, which shows in full color a typical flower cluster and the adjacent foliage, the colors shown being as nearly true to those herein specified as is reasonably possible to obtain by conventional, professional photographic procedures.

DESCRIPTION OF THE NEW PLANT

The following is a detailed description of my new geranium cultivar as observed at my nursery at Stuttgart during the Spring of 1988, with the color designations according to The R.H.S. Colour Chart produced by The Royal Horticultural Society of London, England.

THE PLANT

Origin: Seedling.

Parentage:

*Seed parent.*—'Fledermaus' (U.S. Plant Pat. No. 5,368).

*Pollen parent.*—Unknown.

Classification:

*Botanic.*—*Pelargonium zonale* hybrid.

*Commercial.*—Geranium.

Form: Upright and compact.

Height: Medium; about 35 to 40 cm.

Growth: Vigorous and compact with good strength and a medium growth rate.

Branching character: Normal.

Flower stem length: About 18 cm.

Foliage:

*Quantity.*—Abundant and profusely produced.

*Size of leaf.*—Small; about 8 cm. wide and 5 cm. long.

*Leaf size.*—Reniform with bicrenate margins.

*Texture.*—Smooth.

*Ribs and veins.*—The leaf has five light green veins.

*Color.*—Upper side, light green at the middle and surrounded by dark green zonation. Under side, light green.

THE BUD

Size: Normal.

*Diameter.*—About 9 mm.

*Length.*—About 12 to 15 mm.

Shape: Ovoid with pointed apex.

Opening rate: Medium.

Color petals:

*When sepals first divide.*—Green/White.

*When petals begin to unfurl.*—Light Salmon.

Sepals:

*Number.*—Five.

*Shape.*—Lanceolate.

*Character.*—The sepals stand up when the flowers open.

*Color.*—Inside and outside: Green.

Calyx:

*Shape.*—Flat, like a disc, and no splitting.

THE INFLORESCENCE

Blooming habit: Continuous and profusely from early Spring to late Fall.

Flower cluster:

*Size.*—Large. Diameter — About 11.5 cm. Depth — About 10.5 cm.

*Stalk.*—Length: About 14 cm. Color: Light brown. Character: Upright with good strength.

Number of florets: About sixty-five, closely grouped.

Florets:

*Size.*—Medium.

*Borne.*—Singly on the umbel stems of a cluster.

*Shape.*—When bloom first opens, cup-shaped. When bloom matures, flat.

*Petalage.*—Number of Petals: Seven or eight. Arrangement: Regularly imbricated. Form: Broad with rounded apex and entire margins. Texture: Soft. Aspect: Satiny. Color: Salmon, RHS 41-B/C.

*Petaloids.*—Number: Few. Size: About 4 mm. Color: Salmon.

Discoloration after full bloom: Sometimes there is a slight fading.

Persistence: The flowers are non-shedding and the petals drop off cleanly.

Lasting quality:

*On the plant.*—Thirteen to fourteen days indoors.

REPRODUCTIVE ORGANS

Stamens:

*Number.*—Seven.

*Arrangement.*—In a ring around the ovaries and pistil.

*Anthers.*—Size: About 1.5 mm. Color: White.

*Filaments.*—Length: About 4 to 5 mm. Color: White.

*Pollen.*—Color: Orange.

Pistil:

*Number.*—One.

*Style.*—Length: About 2 to 4 mm. Color: Green.

*Stigma.*—Five cells. Color: White — shining like frosted glass.

Character of ovaries: Normal for Pelargonium.

THE FRUIT

Fertility: The fruit is fertile.

Shape: Ovoid.

Color at muturity: Brown.

A new early and rich flowering variety with salmon colored blooms which provide a very pleasing floral presentation.

I claim:

1. The new and distinct geranium cultivar, substantially as herein shown and described, characterized in particular by the overall salmon coloration of the blooms, the bushy, compact form of the plant, and the abundance of relatively small, darkly zonated leaves having a light green central portion.

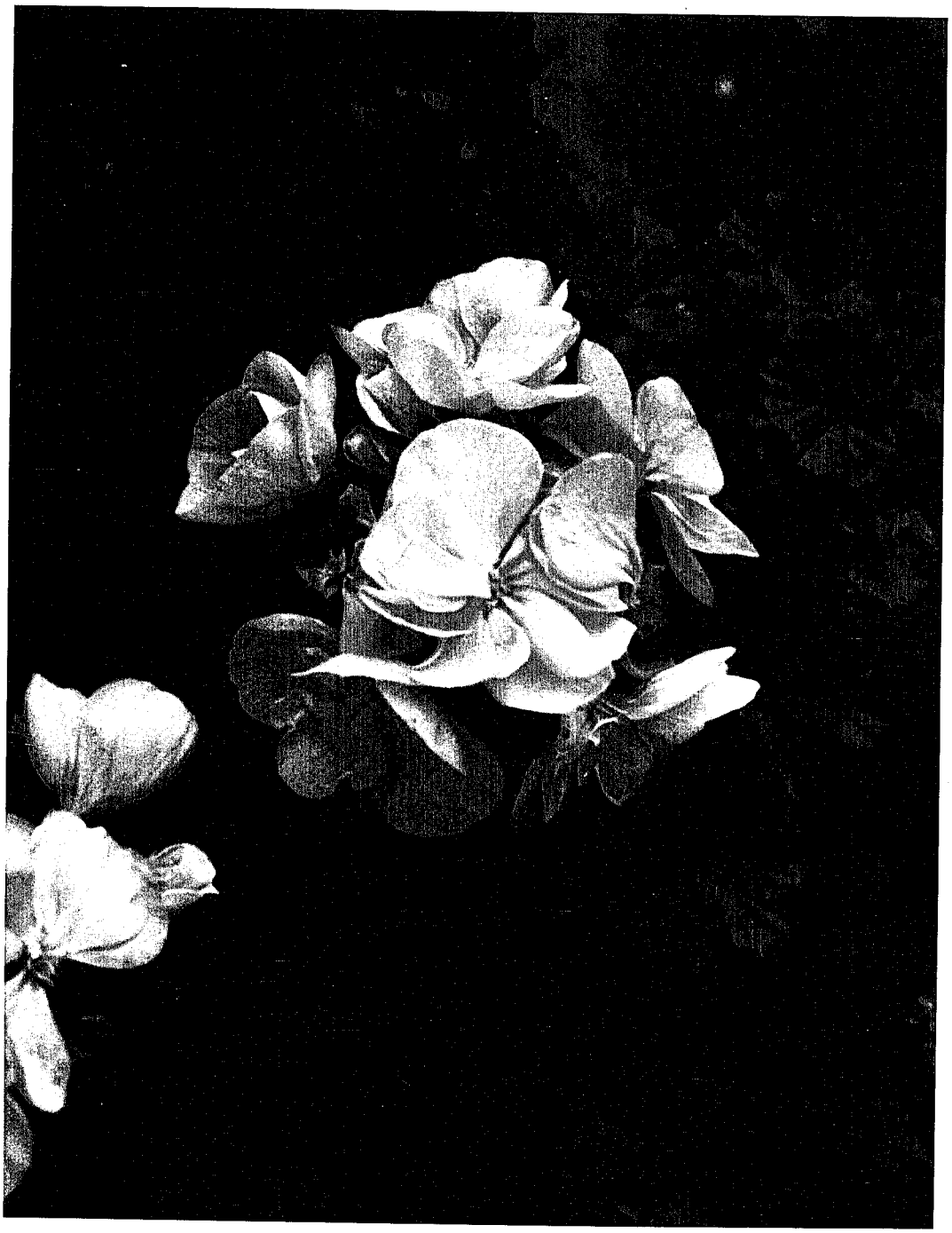

* * * * *